US 7,258,693 B2

(12) United States Patent
Freeman et al.

(10) Patent No.: US 7,258,693 B2
(45) Date of Patent: Aug. 21, 2007

(54) DEVICE AND METHOD FOR VARIABLE SPEED LANCET

(75) Inventors: Dominique M. Freeman, La Honda, CA (US); Dirk Boecker, Palo Alto, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 684 days.

(21) Appl. No.: 10/420,535

(22) Filed: Apr. 21, 2003

(65) Prior Publication Data

US 2004/0010279 A1    Jan. 15, 2004

Related U.S. Application Data

(63) Continuation-in-part of application No. 10/324,053, filed on Dec. 18, 2002, which is a continuation-in-part of application No. 10/127,395, filed on Apr. 19, 2002, now Pat. No. 7,025,774.

(60) Provisional application No. 60/374,304, filed on Apr. 19, 2002.

(51) Int. Cl.
*A61B 17/32* (2006.01)

(52) U.S. Cl. .................. 606/181; 600/583; 128/898

(58) Field of Classification Search ............... 606/167, 606/172, 181, 182, 183; 600/573, 576, 577–579, 600/583; 128/898
See application file for complete search history.

(56) References Cited

U.S. PATENT DOCUMENTS

| | | | |
|---|---|---|---|
| 2,714,890 A | 8/1955 | Vang | 128/305 |
| 3,086,288 A | 4/1963 | Balamuth et al. | 30/272 |
| 3,208,452 A | 9/1965 | Stern | 128/315 |
| 3,358,689 A | 12/1967 | Higgins | 128/329 |
| 3,494,358 A | 2/1970 | Grossenbacher | 128/218 |
| 3,626,929 A | 12/1971 | Sanz | 128/2 R |
| 3,673,475 A | 6/1972 | Britton, Jr. | 318/122 |
| 3,742,954 A | 7/1973 | Strickland | 128/302 |
| 3,832,776 A | 9/1974 | Sawyer | 30/272 |
| 3,953,172 A | 4/1976 | Shapiro | 23/230 |
| 4,077,406 A | 3/1978 | Sandhage et al. | 128/217 |
| 4,154,228 A | 5/1979 | Feldstein et al. | 128/329 |
| 4,203,446 A | 5/1980 | Höfert et al. | 128/329 |
| 4,223,674 A | 9/1980 | Fluent et al. | 128/217 |
| 4,224,125 A | 9/1980 | Nakamura | 204/195 B |
| 4,230,118 A | 10/1980 | Holman et al. | 128/314 |
| 4,340,669 A | 7/1982 | Bauer | 435/14 |

(Continued)

FOREIGN PATENT DOCUMENTS

DE    29824204    10/2000

(Continued)

*Primary Examiner*—Michael J. Hayes
*Assistant Examiner*—Victor Nguyen
(74) *Attorney, Agent, or Firm*—Paul Davis; Heller Ehrman LLP

(57) ABSTRACT

A method of penetrating tissue is provided. The method comprises using a lancet driver to advance a lancet into the tissue; advancing the lancet at a first desired velocity in a first layer of tissue; advancing the lancet at a second desired velocity in a second layer of tissue; and advancing the lancet at a third desired velocity in a third layer of tissue. In one embodiment, the method may including using a processor having logic for controlling velocity of the lancet in each layer of tissue.

34 Claims, 5 Drawing Sheets

U.S. PATENT DOCUMENTS

| | | | |
|---|---|---|---|
| 4,353,984 A | 10/1982 | Yamada | 435/14 |
| 4,356,826 A | 11/1982 | Kubota | 128/630 |
| 4,360,016 A | 11/1982 | Sarrine | 128/763 |
| 4,391,905 A | 7/1983 | Bauer | 435/14 |
| 4,391,906 A | 7/1983 | Bauer | 435/14 |
| 4,414,975 A | 11/1983 | Ryder | 128/314 |
| 4,426,451 A | 1/1984 | Columbus | 436/518 |
| 4,426,884 A | 1/1984 | Polchaninoff | 73/172 |
| 4,449,529 A | 5/1984 | Burns et al. | 128/314 |
| 4,462,405 A | 7/1984 | Ehrlich | 128/329 |
| 4,469,110 A | 9/1984 | Slama | 128/770 |
| 4,517,978 A | 5/1985 | Levin | 128/314 |
| 4,518,384 A | 5/1985 | Tarello et al. | 604/61 |
| 4,535,773 A | 8/1985 | Yoon | 604/51 |
| 4,539,988 A | 9/1985 | Shirley | 128/314 |
| 4,545,382 A | 10/1985 | Higgins | 128/635 |
| 4,553,541 A | 11/1985 | Burns et al. | 128/314 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,595,479 A | 6/1986 | Kimura | 204/294 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,627,445 A | 12/1986 | Garcia et al. | 128/770 |
| 4,637,403 A | 1/1987 | Garcia et al. | 128/770 |
| 4,643,189 A | 2/1987 | Mintz | 128/314 |
| 4,648,408 A | 3/1987 | Hutcheson | 128/770 |
| 4,653,511 A | 3/1987 | Goch | 128/763 |
| 4,653,513 A | 3/1987 | Dombrowski | 128/765 |
| 4,676,244 A | 6/1987 | Enstrom | 128/314 |
| 4,677,979 A | 7/1987 | Burns | 128/314 |
| 4,711,245 A | 12/1987 | Higgins | 128/635 |
| 4,712,548 A | 12/1987 | Enstrom | 128/314 |
| 4,715,374 A | 12/1987 | Maggio | 128/314 |
| 4,735,203 A | 4/1988 | Ryder | 128/314 |
| 4,750,489 A | 6/1988 | Berkman et al. | 128/314 |
| 4,787,398 A | 11/1988 | Garcia et al. | 128/770 |
| 4,794,926 A | 1/1989 | Munsch et al. | 128/314 |
| 4,814,142 A | 3/1989 | Gleisner | 422/56 |
| 4,814,661 A | 3/1989 | Ratzlaff | 310/328 |
| 4,820,010 A | 4/1989 | Sciefres | 385/43 |
| 4,820,399 A | 4/1989 | Senda | 204/403 |
| 4,823,806 A | 4/1989 | Bajada | 128/744 |
| 4,824,639 A | 4/1989 | Hildenbrand | 422/56 |
| RE32,922 E | 5/1989 | Levin | 128/314 |
| 4,827,763 A | 5/1989 | Bourland | 73/172 |
| 4,830,959 A | 5/1989 | McNeill | 435/53 |
| 4,836,904 A | 6/1989 | Armstron | 204/294 |
| 4,844,095 A | 7/1989 | Chiodo | 128/314 |
| 4,850,973 A | 7/1989 | Jordan | 604/157 |
| 4,857,274 A | 8/1989 | Simon | 422/72 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,882,013 A | 11/1989 | Turner | 204/1 |
| 4,883,068 A | 11/1989 | Dechow | 128/760 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,897,173 A | 1/1990 | Nankai | 204/403 |
| 4,900,424 A | 2/1990 | Birch | 204/409 |
| 4,911,794 A | 3/1990 | Parce | 204/1 T |
| 4,920,977 A | 5/1990 | Haynes | 128/770 |
| 4,924,879 A | 5/1990 | O'Brien | 128/770 |
| 4,945,045 A | 7/1990 | Forrest | 435/25 |
| 4,948,727 A | 8/1990 | Cass | 435/18 |
| 4,952,515 A | 8/1990 | Gleisner | 436/169 |
| 4,953,552 A | 9/1990 | DeMarzo | 128/635 |
| 4,966,671 A | 10/1990 | Nylander | 204/153.14 |
| 4,976,724 A | 12/1990 | Nieto | 606/182 |
| 4,983,178 A | 1/1991 | Schnell | |
| 4,990,154 A | 2/1991 | Brown | 606/182 |
| 4,995,402 A | 2/1991 | Smith et al. | 128/771 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,026,388 A | 6/1991 | Ingalz | 606/182 |
| 5,029,583 A | 7/1991 | Meserol et al. | 128/633 |
| 5,035,704 A | 7/1991 | Lambert et al. | 606/182 |
| 5,047,044 A | 9/1991 | Smith et al. | 606/182 |
| 5,054,499 A | 10/1991 | Swierczek | 128/770 |
| 5,059,789 A | 10/1991 | Salcudean | 250/206.1 |
| 5,060,174 A | 10/1991 | Gross | 702/139 |
| 5,070,886 A | 12/1991 | Mitchen | 128/771 |
| 5,074,872 A | 12/1991 | Brown | 606/182 |
| 5,089,112 A | 2/1992 | Skotheim | 204/403 |
| 5,092,842 A | 3/1992 | Bechtold | 604/135 |
| 5,097,810 A | 3/1992 | Fishman et al. | 128/743 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,619 A | 4/1992 | Castro | 422/56 |
| 5,108,564 A | 4/1992 | Szuminsky | 204/153.12 |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,133,730 A | 7/1992 | Biro | 606/182 |
| 5,139,685 A | 8/1992 | Castro | 210/767 |
| 5,141,868 A | 8/1992 | Shanks | 435/288 |
| 5,145,565 A | 9/1992 | Kater et al. | 204/153.1 |
| 5,152,775 A | 10/1992 | Ruppert | 606/182 |
| 5,156,611 A | 10/1992 | Haynes | 606/181 |
| 5,163,442 A | 11/1992 | Ono | 128/760 |
| 5,170,364 A | 12/1992 | Gross | 702/139 |
| D332,490 S | 1/1993 | Brown | D24/146 |
| 5,185,256 A | 2/1993 | Nankai | 435/174 |
| 5,187,100 A | 2/1993 | Matzinger | 436/16 |
| 5,188,118 A | 2/1993 | Terwilliger | 128/753 |
| 5,189,751 A | 3/1993 | Giuliani et al. | 15/22.1 |
| 5,192,415 A | 3/1993 | Yoshioka | 204/403 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,212,879 A | 5/1993 | Biro | 29/437 |
| 5,217,480 A | 6/1993 | Haber | 606/182 |
| 5,222,504 A | 6/1993 | Solomon | 128/744 |
| 5,229,282 A | 7/1993 | Yoshioka | 435/177 |
| 5,230,866 A | 7/1993 | Shartle | 422/103 |
| 5,231,993 A | 8/1993 | Haber et al. | |
| 5,250,066 A | 10/1993 | Lambert | 606/181 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| D342,673 S | 12/1993 | Kataoka | D24/147 |
| 5,272,087 A | 12/1993 | El Murr | 435/291 |
| 5,279,294 A | 1/1994 | Anderson et al. | 128/633 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |
| 5,288,636 A | 2/1994 | Pollman | 435/288 |
| 5,304,192 A | 4/1994 | Crouse | 606/181 |
| 5,304,193 A | 4/1994 | Zhadanov | 606/182 |
| 5,312,590 A | 5/1994 | Gunasingham | 422/56 |
| 5,314,441 A | 5/1994 | Cusack | 606/182 |

| Patent No. | Kind | Date | Name | Class |
|---|---|---|---|---|
| 5,314,442 | A | 5/1994 | Susumu | 606/182 |
| 5,316,012 | A | 5/1994 | Siegal | 128/744 |
| 5,318,583 | A | 6/1994 | Rabenau et al. | |
| 5,320,607 | A | 6/1994 | Ishibashi | 604/115 |
| 5,320,808 | A | 6/1994 | Holen et al. | 422/64 |
| 5,324,302 | A | 6/1994 | Crouse | 606/181 |
| 5,324,303 | A | 6/1994 | Strong | 606/181 |
| 5,332,479 | A | 7/1994 | Uenoyama | 204/153.12 |
| 5,350,392 | A | 9/1994 | Purcell | 606/182 |
| 5,354,287 | A | 10/1994 | Wacks | 604/232 |
| 5,354,447 | A | 10/1994 | Uenoyama | 204/403 |
| 5,356,420 | A | 10/1994 | Czernecki | 606/182 |
| 5,360,410 | A | 11/1994 | Wacks | 604/232 |
| 5,366,469 | A | 11/1994 | Steg | 606/182 |
| 5,366,470 | A | 11/1994 | Ramel | 606/183 |
| 5,366,609 | A | 11/1994 | White | 204/403 |
| 5,368,047 | A | 11/1994 | Suzuki et al. | 128/765 |
| 5,375,397 | A | 12/1994 | Ferrand | 54/66 |
| 5,378,628 | A | 1/1995 | Graetzel | 435/288 |
| 5,382,346 | A | 1/1995 | Uenoyama | 204/403 |
| 5,383,885 | A | 1/1995 | Bland | 606/182 |
| 5,389,534 | A | 2/1995 | Gentezkow | 435/180 |
| 5,393,903 | A | 2/1995 | Graetzel | 556/137 |
| 5,395,387 | A | 3/1995 | Burns | |
| 5,397,334 | A | 3/1995 | Schenk | 606/182 |
| 5,401,376 | A | 3/1995 | Foos | 204/415 |
| 5,402,798 | A | 4/1995 | Swierczek | 128/770 |
| 5,407,545 | A | 4/1995 | Hirose | 204/153.12 |
| 5,407,554 | A | 4/1995 | Saurer | 204/403 |
| 5,407,818 | A | 4/1995 | Gentezkow | 435/180 |
| 5,409,583 | A | 4/1995 | Yoshioka | 204/153.12 |
| 5,410,059 | A | 4/1995 | Fraser | 546/10 |
| 5,415,169 | A | 5/1995 | Siczek et al. | 128/653.1 |
| 5,423,847 | A | 6/1995 | Strong et al. | 606/182 |
| 5,436,161 | A | 7/1995 | Bergstrom | 435/291 |
| 5,437,999 | A | 8/1995 | Diebold | 435/288 |
| 5,443,701 | A | 8/1995 | Willner | 204/153 |
| 5,445,920 | A | 8/1995 | Saito | 430/311 |
| D362,719 | S | 9/1995 | Kaplan | D24/147 |
| 5,454,828 | A | 10/1995 | Schraga | 606/181 |
| 5,456,875 | A | 10/1995 | Lambert | 264/328.1 |
| 5,464,418 | A | 11/1995 | Schraga | 606/182 |
| 5,471,102 | A | 11/1995 | Becker | 310/50 |
| 5,472,427 | A | 12/1995 | Rammler | 604/164 |
| 5,474,084 | A | 12/1995 | Cunniff | 128/744 |
| 5,476,474 | A | 12/1995 | Davis | 606/182 |
| 5,480,387 | A | 1/1996 | Gabriel | 604/134 |
| 5,487,748 | A | 1/1996 | Marshall | 606/182 |
| 5,496,453 | A | 3/1996 | Uenoyama | 205/777.5 |
| 5,498,542 | A | 3/1996 | Corey | 435/283.1 |
| 5,509,410 | A | 4/1996 | Hill | 128/637 |
| 5,510,266 | A | 4/1996 | Bonner et al. | |
| 5,512,159 | A | 4/1996 | Yoshioka | 204/403 |
| 5,514,152 | A | 5/1996 | Smith | 606/182 |
| 5,518,006 | A | 5/1996 | Mawhirt | 128/770 |
| 5,524,636 | A | 6/1996 | Sarvazyan | 128/774 |
| 5,525,511 | A | 6/1996 | D'Costa | 435/287.9 |
| 5,527,333 | A | 6/1996 | Nikkels | 606/182 |
| 5,527,334 | A | 6/1996 | Kanner | 606/182 |
| 5,529,074 | A | 6/1996 | Greenfield | 128/744 |
| 5,540,709 | A | 7/1996 | Ramel | 606/183 |
| 5,543,326 | A | 8/1996 | Heller | 435/287.9 |
| 5,545,174 | A | 8/1996 | Schenk | 606/182 |
| 5,547,702 | A | 8/1996 | Gleisner | 427/2.13 |
| 5,554,166 | A | 9/1996 | Lange | 606/182 |
| 5,558,834 | A | 9/1996 | Chu | 422/55 |
| 5,569,286 | A | 10/1996 | Peckham | 606/181 |
| 5,569,287 | A | 10/1996 | Tezuka | 606/182 |
| 5,571,132 | A | 11/1996 | Mawhirt | 606/182 |
| 5,575,403 | A | 11/1996 | Charlton et al. | 221/31 |
| 5,575,895 | A | 11/1996 | Ikeda | 204/403 |
| 5,582,697 | A | 12/1996 | Ikeda | 204/403 |
| 5,584,846 | A | 12/1996 | Mawhirt | 606/181 |
| 5,593,852 | A | 1/1997 | Heller | 435/14 |
| 5,609,749 | A | 3/1997 | Yamauchi | 205/777.5 |
| 5,613,978 | A | 3/1997 | Harding | 606/181 |
| 5,620,579 | A | 4/1997 | Genshaw | 204/402 |
| 5,624,537 | A | 4/1997 | Turner | 204/403 |
| D379,516 | S | 5/1997 | Rutter | D24/146 |
| 5,628,764 | A | 5/1997 | Schraga | 606/182 |
| 5,628,765 | A | 5/1997 | Morita | 606/182 |
| 5,628,890 | A | 5/1997 | Carter | 204/403 |
| 5,630,986 | A | 5/1997 | Charlton et al. | 422/64 |
| 5,632,410 | A | 5/1997 | Moulton et al. | 221/79 |
| 5,643,306 | A | 7/1997 | Schraga | 606/182 |
| 5,645,555 | A | 7/1997 | Davis | 606/182 |
| 5,650,062 | A | 7/1997 | Ikeda | 205/778 |
| 5,653,863 | A | 8/1997 | Genshaw | 205/777.5 |
| 5,657,760 | A | 8/1997 | Ying et al. | 128/660.03 |
| 5,658,444 | A | 8/1997 | Black | 204/415 |
| 5,662,127 | A | 9/1997 | De Vaughn | 128/765 |
| 5,662,672 | A | 9/1997 | Pambianchi | 606/181 |
| 5,680,872 | A | 10/1997 | Sesekura | 128/760 |
| 5,682,884 | A | 11/1997 | Hill | 128/637 |
| 5,683,562 | A | 11/1997 | Schaffar | 204/403 |
| 5,695,947 | A | 12/1997 | Guo | 435/11 |
| 5,700,695 | A | 12/1997 | Yassinzadeh et al. | 436/180 |
| 5,705,045 | A | 1/1998 | Park | 204/403 |
| 5,708,247 | A | 1/1998 | McAleer | 204/403 |
| 5,709,668 | A | 1/1998 | Wacks | 604/232 |
| 5,710,011 | A | 1/1998 | Forrow | 435/25 |
| 5,714,390 | A | 2/1998 | Hallowitz et al. | 436/526 |
| 5,720,862 | A | 2/1998 | Hamamoto | 204/403 |
| 5,720,924 | A | 2/1998 | Eikmeier et al. | 422/102 |
| D392,391 | S | 3/1998 | Douglas | D24/225 |
| 5,723,284 | A | 3/1998 | Ye | 435/4 |
| 5,727,548 | A | 3/1998 | Hill | 128/637 |
| 5,730,753 | A | 3/1998 | Morita | 606/181 |
| 5,733,300 | A | 3/1998 | Pambianchi | 606/181 |
| D393,716 | S | 4/1998 | Brenneman | D24/147 |
| D393,717 | S | 4/1998 | Brenneman | D24/147 |
| 5,738,244 | A | 4/1998 | Charlton et al. | 221/26 |
| 5,741,634 | A | 4/1998 | Nozoe | 435/4 |
| RE35,803 | E | 5/1998 | Lange | 606/182 |
| 5,746,217 | A | 5/1998 | Erickson | 128/760 |
| 5,755,733 | A | 5/1998 | Morita | 606/182 |
| 5,758,643 | A | 6/1998 | Wong et al. | 128/632 |
| 5,759,364 | A | 6/1998 | Charlton | 204/403 |
| 5,762,770 | A | 6/1998 | Pritchard | 204/403 |
| 5,770,369 | A | 6/1998 | Meade | 435/6 |
| 5,772,586 | A | 6/1998 | Heinonen | 600/300 |
| 5,772,677 | A | 6/1998 | Mawhirt | 606/181 |
| 5,773,270 | A | 6/1998 | D'Orazio | 435/177 |
| 5,776,157 | A | 7/1998 | Thorne et al. | 606/182 |
| 5,776,719 | A | 7/1998 | Douglas | 435/28 |
| 5,782,770 | A | 7/1998 | Mooradian | 600/476 |
| 5,782,852 | A | 7/1998 | Foggia | 606/182 |
| 5,788,651 | A | 8/1998 | Weilandt | 600/567 |
| 5,788,652 | A | 8/1998 | Rahn | 600/577 |
| 5,795,725 | A | 8/1998 | Buechler | 435/7.1 |
| 5,795,774 | A | 8/1998 | Matsumoto | 435/287.9 |
| 5,797,940 | A | 8/1998 | Mawhirt | 606/167 |
| 5,797,942 | A | 8/1998 | Schraga | 606/182 |
| 5,798,030 | A | 8/1998 | Raguse | 204/403 |
| 5,798,031 | A | 8/1998 | Charlton | 204/403 |
| 5,800,781 | A | 9/1998 | Gavin et al. | 422/73 |
| 5,801,057 | A | 9/1998 | Smart et al. | 436/68 |
| 5,810,199 | A | 9/1998 | Charlton et al. | 221/31 |
| 5,820,551 | A | 10/1998 | Hill | 600/347 |
| 5,823,973 | A | 10/1998 | Racchini et al. | 600/573 |
| 5,824,491 | A | 10/1998 | Priest | 435/28 |
| 5,830,219 | A | 11/1998 | Bird et al. | 606/130 |
| 5,840,020 | A | 11/1998 | Heinonen | 600/309 |
| 5,840,171 | A | 11/1998 | Birch | 205/335 |
| 5,846,490 | A | 12/1998 | Yokota et al. | 422/66 |
| 5,849,174 | A | 12/1998 | Sanghera | 205/775 |

| | | | | | | | |
|---|---|---|---|---|---|---|---|
| 5,854,074 | A | 12/1998 | Charlton et al. ............... 436/46 | 6,103,033 | A | 8/2000 | Say ........................... 156/73.1 |
| D403,975 | S | 1/1999 | Douglas ..................... D10/81 | 6,107,083 | A | 8/2000 | Collins ..................... 435/288 |
| 5,855,801 | A | 1/1999 | Lin et al. ........................ 216/2 | 6,117,630 | A | 9/2000 | Reber et al. ................... 435/4 |
| 5,857,983 | A | 1/1999 | Douglas ..................... 600/538 | 6,120,462 | A | 9/2000 | Hibner et al. ............... 600/566 |
| 5,860,922 | A | 1/1999 | Gordon et al. ............... 600/431 | 6,120,676 | A | 9/2000 | Heller ...................... 205/777.5 |
| 5,863,800 | A | 1/1999 | Eikmeier et al. .............. 436/48 | 6,121,009 | A | 9/2000 | Heller ........................... 435/14 |
| 5,866,353 | A | 2/1999 | Berneth ......................... 435/26 | 6,129,823 | A | 10/2000 | Hughes .................. 204/403.01 |
| 5,868,772 | A | 2/1999 | LeVaughn ................... 606/181 | 6,132,449 | A | 10/2000 | Lum et al. .................. 606/181 |
| 5,869,972 | A | 2/1999 | Birch ........................... 342/439 | 6,133,837 | A | 10/2000 | Riley ....................... 340/573.1 |
| 5,871,494 | A | 2/1999 | Simons et al. .............. 606/181 | 6,134,461 | A | 10/2000 | Say ............................. 600/345 |
| 5,872,713 | A | 2/1999 | Douglas ......................... 702/85 | 6,136,013 | A | 10/2000 | Marshall et al. ........... 606/167 |
| 5,873,887 | A | 2/1999 | King ............................ 606/182 | 6,139,562 | A | 10/2000 | Mauze et al. ............... 606/171 |
| 5,876,957 | A | 3/1999 | Douglas ......................... 435/28 | 6,143,164 | A | 11/2000 | Heller et al. .............. 205/777.5 |
| 5,879,311 | A | 3/1999 | Duchon et al. .............. 600/583 | 6,152,942 | A | 11/2000 | Brenneman et al. ........ 606/181 |
| 5,879,373 | A | 3/1999 | Roper .......................... 606/344 | 6,153,069 | A | 11/2000 | Pottgen ....................... 204/403 |
| 5,880,829 | A | 3/1999 | Kauhaniemi et al. ........ 356/246 | RE36,991 | E | 12/2000 | Yamamoto ................... 204/403 |
| 5,882,494 | A | 3/1999 | van Antwerp ............... 204/403 | 6,155,992 | A | 12/2000 | Henning et al. ............. 600/583 |
| 5,885,211 | A | 3/1999 | Eppstein et al. ............. 600/309 | 6,156,051 | A | 12/2000 | Schraga ...................... 606/181 |
| 5,891,053 | A | 4/1999 | Sesekura ..................... 600/583 | 6,157,442 | A | 12/2000 | Raskas .......................... 356/39 |
| 5,900,130 | A | 5/1999 | Benvegnu ................... 204/453 | 6,159,424 | A | 12/2000 | Kauhaniemi et al. ......... 422/63 |
| 5,906,921 | A | 5/1999 | Ikeda ............................ 435/25 | 6,162,611 | A | 12/2000 | Heller ........................... 435/14 |
| D411,619 | S | 6/1999 | Duchon ..................... D24/146 | 6,171,325 | B1 | 1/2001 | Mauze et al. ............... 356/446 |
| 5,916,156 | A | 6/1999 | Hildenbrand ................ 600/347 | 6,175,752 | B1 | 1/2001 | Say ............................. 600/345 |
| 5,916,229 | A | 6/1999 | Evans .......................... 606/171 | 6,176,865 | B1 | 1/2001 | Mauze et al. ............... 606/171 |
| 5,916,230 | A | 6/1999 | Brenneman .................. 606/172 | 6,177,000 | B1 | 1/2001 | Peterson .................... 205/777.5 |
| 5,921,963 | A | 7/1999 | Erez ............................. 604/192 | 6,183,489 | B1 | 2/2001 | Douglas et al. ............. 606/181 |
| 5,922,188 | A | 7/1999 | Ikeda ........................ 204/777.5 | 6,190,612 | B1 | 2/2001 | Berger ...................... 422/82.07 |
| RE36,268 | E | 8/1999 | Szuminsky ................ 205/777.5 | 6,191,852 | B1 | 2/2001 | Paffhausen .................. 356/244 |
| 5,935,075 | A | 8/1999 | Casscells et al. ............ 600/474 | 6,192,891 | B1 | 2/2001 | Gravel ......................... 128/920 |
| 5,938,679 | A | 8/1999 | Freeman et al. ............. 606/181 | 6,193,673 | B1 | 2/2001 | Viola et al. .................. 600/568 |
| 5,951,492 | A | 9/1999 | Douglas ...................... 600/583 | 6,194,900 | B1 | 2/2001 | Freeman ...................... 324/321 |
| 5,951,582 | A | 9/1999 | Thorne et al. ............... 606/182 | 6,197,257 | B1 | 3/2001 | Raskas ...................... 422/82.05 |
| 5,951,836 | A | 9/1999 | McAleer ...................... 204/403 | 6,203,504 | B1 | 3/2001 | Latterell et al. ............. 600/576 |
| 5,954,738 | A | 9/1999 | LeVaughn ................... 606/181 | 6,206,841 | B1 | 3/2001 | Cunningham et al. |
| 5,958,199 | A | 9/1999 | Miyamoto ................... 204/403 | 6,210,420 | B1 | 4/2001 | Mauze et al. ............... 606/182 |
| 5,965,380 | A | 10/1999 | Heller ........................... 435/14 | 6,210,421 | B1 | 4/2001 | Böcker et al. ............... 606/182 |
| 5,968,063 | A | 10/1999 | Chu et al. .................... 606/185 | 6,212,417 | B1 | 4/2001 | Ikeda .................... 204/403.14 |
| 5,971,941 | A | 10/1999 | Simons et al. .............. 600/573 | 6,214,804 | B1 | 4/2001 | Felgner ......................... 514/44 |
| 5,972,199 | A | 10/1999 | Heller ........................ 205/777.5 | 6,221,238 | B1 | 4/2001 | Grundig .................... 205/777.5 |
| 5,983,193 | A | 11/1999 | Heinonen ......................... 705/2 | 6,225,078 | B1 | 5/2001 | Ikeda ........................... 435/25 |
| 5,985,116 | A | 11/1999 | Ikeda ........................... 204/403 | 6,228,100 | B1 | 5/2001 | Schraga ...................... 606/183 |
| 5,993,400 | A | 11/1999 | Rincoe ......................... 600/595 | 6,230,501 | B1 | 5/2001 | Bailey .......................... 62/51.1 |
| 5,997,561 | A | 12/1999 | Böcker et al. ............... 606/182 | 6,231,531 | B1 | 5/2001 | Lum et al. ...................... 601/46 |
| 5,997,817 | A | 12/1999 | Crismore ....................... 422/58 | 6,241,862 | B1 | 6/2001 | McAleer ..................... 204/403 |
| 5,997,818 | A | 12/1999 | Hackner ....................... 422/681 | 6,245,060 | B1 | 6/2001 | Loomis ............................ 606/9 |
| 6,001,067 | A | 12/1999 | Shults .......................... 600/584 | 6,251,260 | B1 | 6/2001 | Heller ....................... 205/777.5 |
| 6,020,110 | A | 2/2000 | Williams ..................... 430/315 | 6,254,831 | B1 | 7/2001 | Barnard .................... 422/82.08 |
| 6,022,324 | A | 2/2000 | Skinner ........................ 600/566 | 6,256,533 | B1 | 7/2001 | Yuzhakov ...................... 604/21 |
| 6,022,366 | A | 2/2000 | Schraga ....................... 606/181 | 6,258,229 | B1 | 7/2001 | Winarta ....................... 204/403 |
| 6,027,459 | A | 2/2000 | Shain et al. ................. 600/573 | 6,258,254 | B1 | 7/2001 | Miyamoto ................. 205/777.5 |
| 6,030,399 | A | 2/2000 | Ignotz .......................... 606/167 | 6,261,241 | B1 | 7/2001 | Burbank et al. ............. 600/564 |
| 6,030,827 | A | 2/2000 | Davis ........................... 435/287 | 6,261,245 | B1 | 7/2001 | Kawai et al. ................. 600/576 |
| 6,033,421 | A | 3/2000 | Theiss .......................... 606/186 | 6,268,161 | B1 | 7/2001 | Han .............................. 435/14 |
| 6,033,866 | A | 3/2000 | Guo .............................. 435/14 | 6,270,637 | B1 | 8/2001 | Crismore .................... 204/403 |
| 6,036,924 | A | 3/2000 | Simons et al. .............. 422/100 | 6,272,359 | B1 | 8/2001 | Kivela ......................... 455/567 |
| 6,048,352 | A | 4/2000 | Douglas et al. ............. 606/181 | 6,281,006 | B1 | 8/2001 | Heller ....................... 435/287.9 |
| D424,696 | S | 5/2000 | Ray ........................... D24/169 | 6,283,926 | B1 | 9/2001 | Cunningham et al. ...... 600/573 |
| 6,060,327 | A | 5/2000 | Keen ............................ 436/518 | 6,283,982 | B1 | 9/2001 | Levaughn .................... 606/172 |
| 6,063,039 | A | 5/2000 | Cunningham ............... 600/573 | 6,284,478 | B1 | 9/2001 | Heller ........................... 435/14 |
| 6,066,296 | A | 5/2000 | Brady ........................... 422/63 | 6,285,448 | B1 | 9/2001 | Kuenstner ..................... 356/39 |
| 6,067,463 | A | 5/2000 | Jeng ............................. 600/336 | 6,285,454 | B1 | 9/2001 | Douglas et al. ............. 356/446 |
| D426,638 | S | 6/2000 | Ray ........................... D24/169 | 6,290,683 | B1 | 9/2001 | Erez ............................. 604/273 |
| 6,071,249 | A | 6/2000 | Cunningham ............... 600/578 | 6,295,506 | B1 | 9/2001 | Heinonen ................... 702/104 |
| 6,071,250 | A | 6/2000 | Douglas ...................... 600/583 | 6,299,757 | B1 | 10/2001 | Feldman ..................... 205/775 |
| 6,071,251 | A | 6/2000 | Cunningham ............... 600/584 | 6,302,855 | B1 | 10/2001 | Lav ............................. 600/584 |
| 6,071,294 | A | 6/2000 | Simons et al. .............. 606/181 | 6,306,104 | B1 | 10/2001 | Cunningham et al. ...... 600/573 |
| 6,074,360 | A | 6/2000 | Haar ............................... 604/57 | 6,306,152 | B1 | 10/2001 | Verdonk et al. ............. 606/182 |
| 6,077,408 | A | 6/2000 | Miyamoto ................... 204/403 | 6,306,347 | B1 | 10/2001 | Mason .......................... 422/58 |
| 6,080,172 | A | 6/2000 | Fujiwara ...................... 606/166 | 6,309,535 | B1 | 10/2001 | Williams ................. 205/777.5 |
| 6,083,710 | A | 7/2000 | Heller ........................... 435/14 | 6,312,612 | B1 | 11/2001 | Sherman .......................... 216/2 |
| 6,086,562 | A | 7/2000 | Jacobsen ...................... 604/156 | 6,315,738 | B1 | 11/2001 | Nishikawa et al. ......... 600/583 |
| 6,090,078 | A | 7/2000 | Erskine ........................ 604/198 | 6,319,210 | B1 | 11/2001 | Douglas et al. ............. 600/583 |
| 6,093,156 | A | 7/2000 | Cunningham et al. ...... 600/573 | 6,322,574 | B1 | 11/2001 | Lloyd .......................... 606/181 |

| Patent No. | Date | Inventor | Class |
|---|---|---|---|
| 6,331,163 B1 | 12/2001 | Kaplan | 600/486 |
| 6,332,871 B1 | 12/2001 | Douglas et al. | 600/583 |
| 6,334,363 B1 | 1/2002 | Testud | 73/862 |
| 6,334,856 B1 | 1/2002 | Allen | 604/191 |
| 6,338,790 B1 | 1/2002 | Feldman | 205/777.5 |
| 6,350,273 B1 | 2/2002 | Minagawa | 606/186 |
| 6,350,451 B1 | 2/2002 | Horn | 424/184.1 |
| 6,352,514 B1 | 3/2002 | Douglas et al. | 600/583 |
| 6,352,523 B1 | 3/2002 | Brown | 604/207 |
| 6,353,753 B1 | 3/2002 | Flock | 600/473 |
| 6,364,889 B1 | 4/2002 | Kheiri et al. | 606/181 |
| 6,364,890 B1 | 4/2002 | Lum et al. | 606/181 |
| 6,375,627 B1 | 4/2002 | Mauze et al. | 600/584 |
| 6,379,301 B1 | 4/2002 | Worthington | 600/309 |
| 6,379,317 B1 | 4/2002 | Kintzig et al. | 600/573 |
| 6,379,324 B1 | 4/2002 | Gartstein | 604/22 |
| 6,379,969 B1 | 4/2002 | Mauze et al. | 436/68 |
| 6,387,709 B1 | 5/2002 | Mason | 436/164 |
| 6,391,005 B1 | 5/2002 | Lum et al. | 604/117 |
| 6,399,394 B1 | 6/2002 | Dahm | 436/180 |
| 6,402,701 B1 | 6/2002 | Kaplan et al. | 600/567 |
| 6,402,704 B1 | 6/2002 | McMorrow | 600/576 |
| 6,409,740 B1 | 6/2002 | Kuhr et al. | 606/182 |
| 6,413,410 B1 | 7/2002 | Hodges | 205/775 |
| 6,413,411 B1 | 7/2002 | Pottgen | 205/777.5 |
| 6,421,633 B1 | 7/2002 | Heinonen | 703/11 |
| 6,428,664 B1 | 8/2002 | Bhullar | 204/403.03 |
| 6,436,256 B1 | 8/2002 | Williams | 204/403.06 |
| 6,436,721 B1 | 8/2002 | Kuo | 436/514 |
| 6,440,645 B1 | 8/2002 | Yon-Hin | 430/322 |
| 6,451,040 B1 | 9/2002 | Purcell | 606/181 |
| 6,458,258 B2 | 10/2002 | Taniike | 204/403 |
| 6,461,496 B1 | 10/2002 | Feldman et al. | 205/777.5 |
| 6,462,162 B2 | 10/2002 | van Antwerp | 528/77 |
| 6,471,903 B2 | 10/2002 | Sherman | 264/328.1 |
| 6,472,220 B1 | 10/2002 | Simons et al. | 436/63 |
| 6,475,436 B1 | 11/2002 | Schabbach | 422/64 |
| 6,475,750 B1 | 11/2002 | Han | 435/14 |
| 6,484,046 B1 | 11/2002 | Say | 600/345 |
| 6,485,439 B1 | 11/2002 | Roe et al. | 600/578 |
| 6,488,891 B2 | 12/2002 | Mason et al. | 422/58 |
| 6,489,052 B1 | 12/2002 | Acker | 600/584 |
| 6,491,709 B2 | 12/2002 | Sharma et al. | 606/181 |
| 6,497,845 B1 | 12/2002 | Sacherer | 422/104 |
| 6,501,404 B2 | 12/2002 | Walker | 341/143 |
| 6,503,210 B1 | 1/2003 | Hirao et al. | 600/576 |
| 6,503,231 B1 | 1/2003 | Prausnitz | 604/272 |
| 6,506,168 B1 | 1/2003 | Fathallah | 600/578 |
| 6,506,575 B1 | 1/2003 | Knappe et al. | 435/25 |
| 6,508,785 B1 | 1/2003 | Eppstein | 604/113 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,527,778 B2 | 3/2003 | Athanasiou | 606/80 |
| 6,530,892 B1 | 3/2003 | Kelly | |
| 6,530,937 B1 | 3/2003 | Schraga | 606/182 |
| 6,533,949 B1 | 3/2003 | Yeshurun | 216/11 |
| 6,537,242 B1 | 3/2003 | Palmer | 604/22 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller | 205/777.5 |
| 6,555,061 B1 | 4/2003 | Leong | 422/58 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,561,989 B2 | 5/2003 | Whitson | 600/573 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,574,490 B2 | 6/2003 | Abbink | 600/316 |
| 6,576,101 B1 | 6/2003 | Heller | 204/403.14 |
| 6,576,416 B2 | 6/2003 | Haviland | 435/4 |
| 6,587,705 B1 | 7/2003 | Kim | 600/347 |
| 6,589,260 B1 | 7/2003 | Schmelzeisen-Redeker | 606/181 |
| 6,589,261 B1 | 7/2003 | Abulhaj | 606/181 |
| 6,591,125 B1 | 7/2003 | Buse | 600/347 |
| 6,592,745 B1 | 7/2003 | Feldman | 205/777.5 |
| 6,599,407 B2 | 7/2003 | Taniike | 204/403.1 |
| 6,599,693 B1 | 7/2003 | Webb | 435/4 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,607,658 B1 | 8/2003 | Heller | 205/777.5 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,623,501 B2 | 9/2003 | Heller | 606/181 |
| 6,626,851 B2 | 9/2003 | Hirao | 600/576 |
| 6,635,222 B2 | 10/2003 | Kent | 422/22 |
| 6,641,533 B2 | 11/2003 | Causey, III | 600/300 |
| 6,645,368 B1 | 11/2003 | Beatty | 205/792 |
| 6,652,720 B1 | 11/2003 | Mansouri | 204/403.11 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,671,527 B2 | 12/2003 | Peterson | 600/316 |
| 6,679,841 B2 | 1/2004 | Bojan | 600/309 |
| 6,679,852 B1 | 1/2004 | Schmelzeisen-Redeker | 600/583 |
| 6,706,000 B2 | 3/2004 | Perez | 600/583 |
| 6,706,159 B2 | 3/2004 | Moerman | 204/403.03 |
| 6,706,232 B2 | 3/2004 | Hasegawa | 264/403.09 |
| 6,713,660 B2 | 3/2004 | Roe | 604/361 |
| 6,719,887 B2 | 4/2004 | Hasegawa | 204/403.09 |
| 6,719,923 B2 | 4/2004 | Stiene | 252/511 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,733,493 B2 | 5/2004 | Gruzdev | 606/9 |
| 6,736,777 B2 | 5/2004 | Kim | 600/365 |
| 6,740,215 B1 | 5/2004 | Nakaminami | 204/403.14 |
| 6,743,211 B1 | 6/2004 | Prausnitz | 604/239 |
| 6,749,792 B2 | 6/2004 | Olsen | 264/328.1 |
| 6,751,491 B2 | 6/2004 | Lew | 600/345 |
| 6,752,817 B2 | 6/2004 | Flora | 606/181 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |

| | | | | | | | |
|---|---|---|---|---|---|---|---|
| 6,801,804 B2 | 10/2004 | Miller | 604/20 | 2002/0188224 A1 | 12/2002 | Roe | 600/584 |
| 6,802,199 B2 | 10/2004 | Hilgers | 72/370.1 | 2003/0018282 A1 | 1/2003 | Effenhauser | 600/583 |
| 6,802,811 B1 | 10/2004 | Slepian | 600/309 | 2003/0018300 A1 | 1/2003 | Duchon | 604/164.01 |
| 6,802,957 B2 | 10/2004 | Jung | 205/777.5 | 2003/0028126 A1 | 2/2003 | List | 600/583 |
| 6,805,780 B1 | 10/2004 | Ryu | 204/403.01 | 2003/0050573 A1 | 3/2003 | Kuhr | 600/567 |
| 6,808,908 B2 | 10/2004 | Yao | 435/181 | 2003/0050656 A1 | 3/2003 | Schraga | 606/182 |
| 6,808,937 B2 | 10/2004 | Ligler | 436/518 | 2003/0060730 A1 | 3/2003 | Perez | 600/576 |
| 6,809,807 B1 | 10/2004 | Erickson | 356/213 | 2003/0073089 A1 | 4/2003 | Mauze | 435/6 |
| 6,811,557 B2 | 11/2004 | Schraga | 606/182 | 2003/0073229 A1 | 4/2003 | Greenstein | 435/287.2 |
| 6,811,659 B2 | 11/2004 | Vachon | 204/224 | 2003/0073931 A1 | 4/2003 | Boecker | 600/573 |
| 6,811,753 B2 | 11/2004 | Hirao | 422/101 | 2003/0083685 A1 | 5/2003 | Freeman et al. | |
| 6,811,792 B2 | 11/2004 | Roser | 424/423 | 2003/0083686 A1 | 5/2003 | Freeman | 606/181 |
| 6,812,031 B1 | 11/2004 | Carlsson | 436/52 | 2003/0088191 A1 | 5/2003 | Freeman et al. | 600/583 |
| 6,814,843 B1 | 11/2004 | Bhullar | 204/403.01 | 2003/0089730 A1 | 5/2003 | May | 221/232 |
| 6,814,844 B2 | 11/2004 | Bhullar | 204/403.1 | 2003/0093010 A1 | 5/2003 | Essenpreis | 600/583 |
| 6,814,845 B2 | 11/2004 | Wilson | 204/486 | 2003/0100040 A1 | 5/2003 | Bonnecaze | 435/14 |
| 6,815,186 B2 | 11/2004 | Clark | 435/183 | 2003/0106810 A1 | 6/2003 | Douglas | 205/777.5 |
| 6,816,742 B2 | 11/2004 | Kim | 600/345 | 2003/0109777 A1 | 6/2003 | Kloepfer | 600/367 |
| 6,818,180 B2 | 11/2004 | Douglas | 422/58 | 2003/0111357 A1 | 6/2003 | Black | 205/775 |
| 6,821,483 B2 | 11/2004 | Phillips | 422/58 | 2003/0113827 A1 | 6/2003 | Burkoth | 435/14 |
| 6,823,750 B2 | 11/2004 | Hodges | 73/864.72 | 2003/0116447 A1 | 6/2003 | Sturridge | 205/777.5 |
| 6,825,047 B1 | 11/2004 | Woudenberg | 436/518 | 2003/0135333 A1 | 7/2003 | Aceti | 702/31 |
| 6,827,250 B2 | 12/2004 | Uhland | 228/110.1 | 2003/0143113 A2 | 7/2003 | Yuzhakov | 422/56 |
| 6,827,829 B2 | 12/2004 | Kawanaka | 204/403.02 | 2003/0144608 A1 | 7/2003 | Kojima | 600/583 |
| 6,830,551 B1 | 12/2004 | Uchigaki | 600/584 | 2003/0144609 A1 | 7/2003 | Kennedy | 600/583 |
| 6,830,668 B2 | 12/2004 | Musho | 204/400 | 2003/0146110 A1 | 8/2003 | Karinka | 205/777.5 |
| 6,830,669 B2 | 12/2004 | Miyazaki | 204/409 | 2003/0149348 A1 | 8/2003 | Raskas | 600/310 |
| 6,833,540 B2 | 12/2004 | MacKenzie | 250/214 | 2003/0149377 A1 | 8/2003 | Erickson | 600/573 |
| 6,835,184 B1 | 12/2004 | Sage | 604/46 | 2003/0153900 A1 | 8/2003 | Aceti | 604/890.1 |
| 6,835,553 B2 | 12/2004 | Han | 435/14 | 2003/0191415 A1 | 10/2003 | Moerman | 600/584 |
| 6,837,858 B2 | 1/2005 | Cunningham | 600/573 | 2003/0195435 A1 | 10/2003 | Williams | 600/583 |
| 6,837,976 B2 | 1/2005 | Cai | 204/403.14 | 2003/0195540 A1 | 10/2003 | Moerman | 606/181 |
| 6,837,988 B2 | 1/2005 | Leong | 205/792 | 2003/0199744 A1 | 10/2003 | Buse | 600/347 |
| 6,840,912 B2 | 1/2005 | Kloepfer | 600/583 | 2003/0199789 A1 | 10/2003 | Boecker | 600/575 |
| 6,841,052 B2 | 1/2005 | Musho | 204/401 | 2003/0199790 A1 | 10/2003 | Boecker | 600/576 |
| 6,843,254 B2 | 1/2005 | Tapper | 128/898 | 2003/0199791 A1 | 10/2003 | Boecker | 600/576 |
| 6,847,451 B2 | 1/2005 | Pugh | 356/436 | 2003/0199891 A1 | 10/2003 | Argauer | 606/181 |
| 6,849,168 B2 | 2/2005 | Crumly | 204/416 | 2003/0199893 A1 | 10/2003 | Boecker | 606/181 |
| 6,849,216 B2 | 2/2005 | Rappin | 264/134 | 2003/0199894 A1 | 10/2003 | Boecker | 606/181 |
| 6,850,790 B2 | 2/2005 | Berner | 600/347 | 2003/0199896 A1 | 10/2003 | Boecker | 606/181 |
| 2001/0017269 A1 | 8/2001 | Heller | 205/777.5 | 2003/0199897 A1 | 10/2003 | Boecker | 606/181 |
| 2001/0027328 A1 | 10/2001 | Lum | 606/186 | 2003/0199898 A1 | 10/2003 | Boecker | 606/181 |
| 2001/0031931 A1 | 10/2001 | Cunningham et al. | 600/573 | 2003/0199899 A1 | 10/2003 | Boecker | 606/181 |
| 2001/0054319 A1 | 12/2001 | Heller | 73/849 | 2003/0199900 A1 | 10/2003 | Boecker | 606/181 |
| 2002/0002344 A1 | 1/2002 | Douglas et al. | 600/583 | 2003/0199901 A1 | 10/2003 | Boecker | 606/181 |
| 2002/0004196 A1 | 1/2002 | Whitson | 435/4 | 2003/0199902 A1 | 10/2003 | Boecker | 606/181 |
| 2002/0025469 A1 | 2/2002 | Heller | 429/43 | 2003/0199903 A1 | 10/2003 | Boecker | 606/181 |
| 2002/0029058 A1 | 3/2002 | Levaughn | 606/181 | 2003/0199904 A1 | 10/2003 | Boecker | 606/181 |
| 2002/0040230 A1 | 4/2002 | Kuhr | 606/181 | 2003/0199905 A1 | 10/2003 | Boecker | 606/181 |
| 2002/0042090 A1 | 4/2002 | Heller | 435/14 | 2003/0199906 A1 | 10/2003 | Boecker | 606/181 |
| 2002/0044890 A1 | 4/2002 | Black | 422/56 | 2003/0199907 A1 | 10/2003 | Boecker | 606/181 |
| 2002/0052618 A1 | 5/2002 | Haar et al. | 606/181 | 2003/0199908 A1 | 10/2003 | Boecker | 606/181 |
| 2002/0053523 A1 | 5/2002 | Liamos | 205/787 | 2003/0199909 A1 | 10/2003 | Boecker | 606/181 |
| 2002/0057993 A1 | 5/2002 | Maisey | 422/82.01 | 2003/0199910 A1 | 10/2003 | Boecker | 606/181 |
| 2002/0076349 A1 | 6/2002 | Aitken | 422/58 | 2003/0199911 A1 | 10/2003 | Boecker | 606/181 |
| 2002/0078091 A1 | 6/2002 | Vu | 707/513 | 2003/0199912 A1 | 10/2003 | Pugh | 606/182 |
| 2002/0081588 A1 | 6/2002 | Lumley-Woodyear | 435/6 | 2003/0201194 A1 | 10/2003 | Heller | 205/777.5 |
| 2002/0082543 A1 | 6/2002 | Park et al. | 604/21 | 2003/0203352 A1 | 10/2003 | Haviland | 435/4 |
| 2002/0084196 A1 | 7/2002 | Liamos | 205/792 | 2003/0206828 A1 | 11/2003 | Bell | 422/44 |
| 2002/0087056 A1 | 7/2002 | Aceti | | 2003/0208140 A1 | 11/2003 | Pugh | 600/584 |
| 2002/0092612 A1 | 7/2002 | Davies | 156/292 | 2003/0212344 A1 | 11/2003 | Yuzhakov | 600/583 |
| 2002/0103499 A1 | 8/2002 | Perez et al. | 606/182 | 2003/0212345 A1 | 11/2003 | McAllister | 600/584 |
| 2002/0120216 A1 | 8/2002 | Fritz | 600/583 | 2003/0212346 A1 | 11/2003 | McAllister | 600/584 |
| 2002/0130042 A1 | 9/2002 | Moerman | 204/403.01 | 2003/0212347 A1 | 11/2003 | Sohrab | 600/584 |
| 2002/0136667 A1 | 9/2002 | Subramanian | 422/100 | 2003/0212423 A1 | 11/2003 | Pugh | 606/181 |
| 2002/0136863 A1 | 9/2002 | Subramanian | 428/156 | 2003/0212424 A1 | 11/2003 | Briggs | 606/181 |
| 2002/0137998 A1 | 9/2002 | Smart | 600/347 | 2003/0216767 A1 | 11/2003 | List | 606/181 |
| 2002/0148739 A2 | 10/2002 | Liamos | 205/787 | 2003/0217918 A1 | 11/2003 | Davies | 204/403.14 |
| 2002/0160520 A1 | 10/2002 | Orloff | 436/72 | 2003/0220552 A1 | 11/2003 | Reghabi | 600/365 |
| 2002/0161289 A1 | 10/2002 | Hopkins | 600/322 | 2003/0220663 A1 | 11/2003 | Fletcher | 606/182 |
| 2002/0168290 A1 | 11/2002 | Yuzhakov | 422/56 | 2003/0223906 A1 | 12/2003 | McAllister | 422/58 |
| 2002/0176984 A1 | 11/2002 | Smart | 428/336 | 2003/0225429 A1 | 12/2003 | Garthe | 606/182 |
| 2002/0177761 A1 | 11/2002 | Orloff | 600/309 | 2003/0225430 A1 | 12/2003 | Schraga | 606/182 |

| Pub. No. | Date | Inventor | Class |
|---|---|---|---|
| 2003/0228637 A1 | 12/2003 | Wang | 435/7.9 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0026243 A1 | 2/2004 | Davies | 204/403.14 |
| 2004/0030353 A1 | 2/2004 | Schmelzeisen | 606/201 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0049220 A1 | 3/2004 | Boecker | 606/181 |
| 2004/0054267 A1 | 3/2004 | Feldman | 600/316 |
| 2004/0054898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0092995 A1 | 5/2004 | Boecker | 606/181 |
| 2004/0096991 A1 | 5/2004 | Zhang | 436/518 |
| 2004/0098010 A1 | 5/2004 | Davison | 606/181 |
| 2004/0102803 A1 | 5/2004 | Boecker | 606/183 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0115754 A1 | 6/2004 | Chang | 435/14 |
| 2004/0115831 A1 | 6/2004 | Meathrel | 436/514 |
| 2004/0116829 A1 | 6/2004 | Raney | 600/573 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Keheiri | 606/182 |
| 2004/0167383 A1 | 8/2004 | Kim | 600/365 |
| 2004/0171057 A1 | 9/2004 | Yang | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koilke | 606/181 |
| 2004/0193201 A1 | 9/2004 | Kim | 606/181 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/792 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Schraga | 606/181 |
| 2004/0238357 A1 | 12/2004 | Bhullar | 204/400 |
| 2004/0238358 A1 | 12/2004 | Forrow | 204/403 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |

| Pub. No. | Date | Name | Class |
|---|---|---|---|
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |

FOREIGN PATENT DOCUMENTS

| | | |
|---|---|---|
| DE | 10032042 | 1/2002 |
| DE | 10057832 | 2/2002 |
| DE | 10142232 | 3/2003 |
| EP | 0289 269 | 11/1988 |
| EP | 0320109 | 6/1989 |
| EP | 0170375 | 5/1990 |
| EP | 0136362 | 12/1990 |
| EP | 0453283 | 10/1991 |
| EP | 0374355 | 6/1993 |
| EP | 0351891 | 9/1993 |
| EP | 0593096 | 4/1994 |
| EP | 0415388 | 5/1995 |
| EP | 0505494 | 7/1995 |
| EP | 0359831 | 8/1995 |
| EP | 0471986 | 10/1995 |
| EP | 0368474 | 12/1995 |
| EP | 0461601 | 12/1995 |
| EP | 0429076 | 1/1996 |
| EP | 0552223 | 7/1996 |
| EP | 0735363 | 10/1996 |
| EP | 0505504 | 3/1997 |
| EP | 0406304 | 8/1997 |
| EP | 0537761 | 8/1997 |
| EP | 0795601 | 9/1997 |
| EP | 0562370 | 11/1997 |
| EP | 0415393 | 12/1997 |
| EP | 0560336 | 5/1998 |
| EP | 0878 708 | 11/1998 |
| EP | 0505475 | 3/1999 |
| EP | 0901018 | 3/1999 |
| EP | 0470649 | 6/1999 |
| EP | 0847447 | 11/1999 |
| EP | 0964059 | 12/1999 |
| EP | 0969097 | 1/2000 |
| EP | 1021950 | 7/2000 |
| EP | 0894869 | 2/2001 |
| EP | 1074832 | 2/2001 |
| EP | 1093854 | 4/2001 |
| EP | 1114995 | 7/2001 |
| EP | 0736607 | 8/2001 |
| EP | 0730037 | 12/2001 |
| EP | 0636879 | 1/2002 |
| EP | 0851224 | 3/2002 |
| EP | 0856586 | 5/2002 |
| EP | 0817809 | 7/2002 |
| EP | 0872728 | 7/2002 |
| EP | 0795748 | 8/2002 |
| EP | 0685737 | 9/2002 |
| EP | 0880692 | 1/2004 |
| EP | 1246688 | 5/2004 |
| GB | 2168815 | 6/1986 |
| JP | 2-326247 | 11/1990 |
| JP | 10-296325 | 10/1998 |
| WO | WO80/01389 | 7/1980 |
| WO | WO85/04089 | 9/1985 |
| WO | WO86/07632 | 12/1985 |
| WO | WO91/09139 | 6/1991 |
| WO | WO93/06979 | 4/1993 |
| WO | WO93/25898 | 12/1993 |
| WO | WO94/27140 | 11/1994 |
| WO | WO94/29703 | 12/1994 |
| WO | WO94/29704 | 12/1994 |
| WO | WO94/29731 | 12/1994 |
| WO | WO95/00662 | 1/1995 |
| WO | WO95/10223 | 4/1995 |
| WO | WO95/22597 | 8/1995 |
| WO | WO96/30431 | 10/1996 |
| WO | WO97/02359 | 1/1997 |
| WO | WO97/02487 | 1/1997 |
| WO | WO97/18464 | 5/1997 |
| WO | WO97/30344 | 8/1997 |
| WO | WO97/42882 | 11/1997 |
| WO | WO97/42888 | 11/1997 |
| WO | WO97/45720 | 12/1997 |
| WO | WO98/03431 | 1/1998 |
| WO | WO98/19159 | 5/1998 |
| WO | WO98/20332 | 5/1998 |
| WO | WO98/20348 | 5/1998 |
| WO | WO98/24366 | 6/1998 |
| WO | WO98/35225 | 8/1998 |
| WO | WO99/03584 | 1/1999 |
| WO | WO99/05966 | 2/1999 |
| WO | WO99/13100 | 3/1999 |
| WO | WO99/19507 | 4/1999 |
| WO | WO99/19717 | 4/1999 |
| WO | WO99/27852 | 6/1999 |
| WO | WO99/62576 | 12/1999 |
| WO | WO99/64580 | 12/1999 |
| WO | WO 00/09184 | 2/2000 |
| WO | WO 00/30186 | 5/2000 |
| WO | WO 00/39914 | 7/2000 |
| WO | WO 00/44084 | 7/2000 |
| WO | WO 00/50771 | 8/2000 |
| WO | WO 00/60340 | 10/2000 |
| WO | WO 00/64022 | 10/2000 |
| WO | WO 00/67245 | 11/2000 |
| WO | WO 00/67268 | 11/2000 |
| WO | WO 01/00090 | 1/2001 |
| WO | WO 01/00090 A1 | 1/2001 |
| WO | WO 01/75433 | 3/2001 |
| WO | WO 01/23885 | 4/2001 |
| WO | WO 01/25775 | 4/2001 |
| WO | WO 01/26813 | 4/2001 |
| WO | WO 01/33216 | 5/2001 |
| WO | WO 01/34029 | 5/2001 |
| WO | WO 01/36955 | 5/2001 |
| WO | WO 01/40788 | 7/2001 |
| WO | WO 01/57510 | 8/2001 |
| WO | WO 01/64105 | 9/2001 |
| WO | WO 01/66010 | 9/2001 |
| WO | WO 01/66010 A1 | 9/2001 |
| WO | WO 01/72225 | 10/2001 |
| WO | WO 01/73124 | 10/2001 |
| WO | WO 01/73395 | 10/2001 |

| | | | | | | |
|---|---|---|---|---|---|---|
| WO | WO 01/89691 | 11/2001 | | WO | WO 03/000321 | 1/2003 |
| WO | WO 02/00101 | 1/2002 | | WO | WO 03/023389 | 3/2003 |
| WO | WO 02/02796 | 1/2002 | | WO | WO 03/042691 | 5/2003 |
| WO | WO 02/08750 | 1/2002 | | WO | WO 03/045557 | 6/2003 |
| WO | WO 02/08753 | 1/2002 | | WO | WO 03/046542 | 6/2003 |
| WO | WO 02/08950 | 1/2002 | | WO | WO 03/049609 | 6/2003 |
| WO | WO 02/18940 | 3/2002 | | WO | WO 03/050534 | 6/2003 |
| WO | WO 02/32559 | 4/2002 | | WO | WO 03/066128 | 8/2003 |
| WO | WO 02/41779 | 5/2002 | | WO | WO 03/070099 | 8/2003 |
| WO | WO 02/44948 | 6/2002 | | WO | WO 03/071940 | 9/2003 |
| WO | WO 02/056769 A1 | 7/2002 | | WO | WO 2004/008130 | 1/2004 |
| WO | WO 02/059734 | 8/2002 | | WO | WO 2004/026130 | 4/2004 |
| WO | WO 02/069791 | 9/2002 | | WO | WO 2004/041082 | 5/2004 |
| WO | WO 02/077638 | 10/2002 | | WO | WO 2004/054455 | 7/2004 |
| WO | WO 02/100251 | 12/2002 | | WO | WO 2004/060174 | 7/2004 |
| WO | WO 02/100252 | 12/2002 | | WO | WO 2004/060446 | 7/2004 |
| WO | WO 02/100253 | 12/2002 | | WO | WO 2004/091693 | 10/2004 |
| WO | WO 02/100254 | 12/2002 | | WO | WO 2004/107964 | 12/2004 |
| WO | WO 02/100460 | 12/2002 | | WO | WO 2004/107975 | 12/2004 |
| WO | WO 02/100461 | 12/2002 | | WO | WO 2004/112602 | 12/2004 |
| WO | WO 02/101343 | 12/2002 | | WO | WO 2005/001418 | 1/2005 |
| WO | WO 02/101359 | 12/2002 | | | | |

…
DEVICE AND METHOD FOR VARIABLE SPEED LANCET

RELATED APPLICATIONS

This application is continuation in part of commonly assigned, U.S. patent application Ser. No. 10/324,053 filed Dec. 18, 2002, which is a continuation-in-part of U.S. Patent application titled "Tissue Penetration Device" 10/127,395 filed on Apr. 19, 2002 now U.S. Pat. No. 7,025,774. The present application claims the benefit of priority to U.S. Provisional Patent Application Ser. No. 60/374,304 filed Apr. 19,2002 and U.S. Patent Application titled "Sampling Module Device and Method" 10/127,201 filed on Apr. 19, 2002. The present application is also related to U.S. patent applications Ser. No. 10/335,142 through 10/335,182 filed Dec. 31, 2002. The present application is also related to PCT Application PCT/US03/40095 filed on Apr. 21, 2003. All applications listed above are incorporated herein by reference in their entirety for all purposes.

BACKGROUND

Lancing devices are known in the medical health-care products industry for piercing the skin to produce blood for analysis. Typically, a drop of blood for analysis is obtained by launching or driving a lancet into tissue to create a small incision, which generates a small blood droplet on the tissue surface.

Current mechanical lancet launchers are configured to actuate ballistically. The lancet is driven out from the opening in the launcher and when a predetermined penetration depth is reached, a return spring propels the lancet back into the housing with roughly the same velocity as for the inbound. There is no mechanism to control the lancet in flight (inbound or outbound) other than a hard stop for maximum penetration. It is therefore impossible to control lancet velocity for skin properties, let alone skin anatomy differences, in these devices other than a crude depth setting. Known launchers may use stepped offsets in a range of 0.9 mm to 2.3 mm or switchable end caps to attempt to control lancet depth. The thicker the offset, the shallower the resulting penetration. These depth settings are, in actuality, a measurement of the protrusion of the lancet tip from the housing, and do not reflect the actual penetration depth of the lancet because of tenting or bending of skin before or during cutting. Unfortunately, without reliable lancet control during actuation, the pain and other drawbacks associated with using known mechanical lancet launchers discourage patients from following a structured glucose monitoring regime.

SUMMARY OF THE INVENTION

The present invention provides solutions for at least some of the drawbacks discussed above. Specifically, some embodiments of the present invention provide improved control of lancet or penetrating member velocity. At least some of these and other objectives described herein will be met by embodiments of the present invention.

In one aspect of the present invention, a method of penetrating tissue is provided. The method comprises using a lancet driver to advance a lancet into the tissue; advancing the lancet at a first desired velocity in a first layer of tissue; advancing the lancet at a second desired velocity in a second layer of tissue; and advancing the lancet at a third desired velocity in a third layer of tissue. In one embodiment, the method may including using a processor having logic for controlling velocity of the lancet in each layer of tissue. In another embodiment, the first velocity is at least partially determined based on hydration of the stratum corneum. It should also be understood that the lancet driver may be electromechanical. The velocity may be determined based on cell population and distribution in the different zones of tissue. The processor may also determine what proportion of electrical power consumption is related to the stratum corneum by measuring differences between normal and hydrated stratum corneum.

In another embodiment according to the present invention, a method is provided for penetrating tissue. The method comprises using a drive force generator to advance a penetrating member along a penetration path into the tissue wherein the penetrating member having a penetrating member velocity equal to a first velocity in a first layer of tissue. Penetrating member velocity is determined at a plurality of locations along the penetration path. The method also includes adjusting penetrating member velocity at a plurality of locations along the penetration path prior to the penetrating member coming to a stop in the tissue. In another embodiment, the method may further include advancing the penetrating member at a maximum velocity through the stratum corneum, at a velocity in the epidermis sufficient to reduce shock waves to pain sensor in dermis, and at a velocity in the dermis is sufficient for efficient cutting of blood vessels without stimulating pain sensors.

In another aspect of the present invention, a lancing system is provided fto drive a lancet during a lancing cycle and for use on a tissue site. The system comprises a lancet driver; a processor coupled to said lancet driver, the processor configured to adjust lancet velocity to achieve a desired velocity based on the layer of tissue through which the lancet is cutting. The system may include a user interface allowing a user to adjust penetration depth based on stratum corneum hydration. The user interface may also allow a user to adjust lancet velocity based on user pain. The system may also include memory for storing at least one of the following to determine a skin profile: energy consumed per lancing event; time of day of. In a still further aspect of the present invention, a further method of driving a lancet into a tissue site is provided. The method comprises calculating stratum corneum thickness based on energy consumed and depth of lancet penetration on a previous lancing cycle; driving the lancet into the tissue site, wherein the lancet does not penetrate more than a desired distance beyond the stratum corneum thickness, the stratum corneum thickness determined by an inflection point of energy consumption when the lancet exits that layer.

A further understanding of the nature and advantages of the invention will become apparent by reference to the remaining portions of the specification and drawings.

DESCRIPTION

Figure 1:
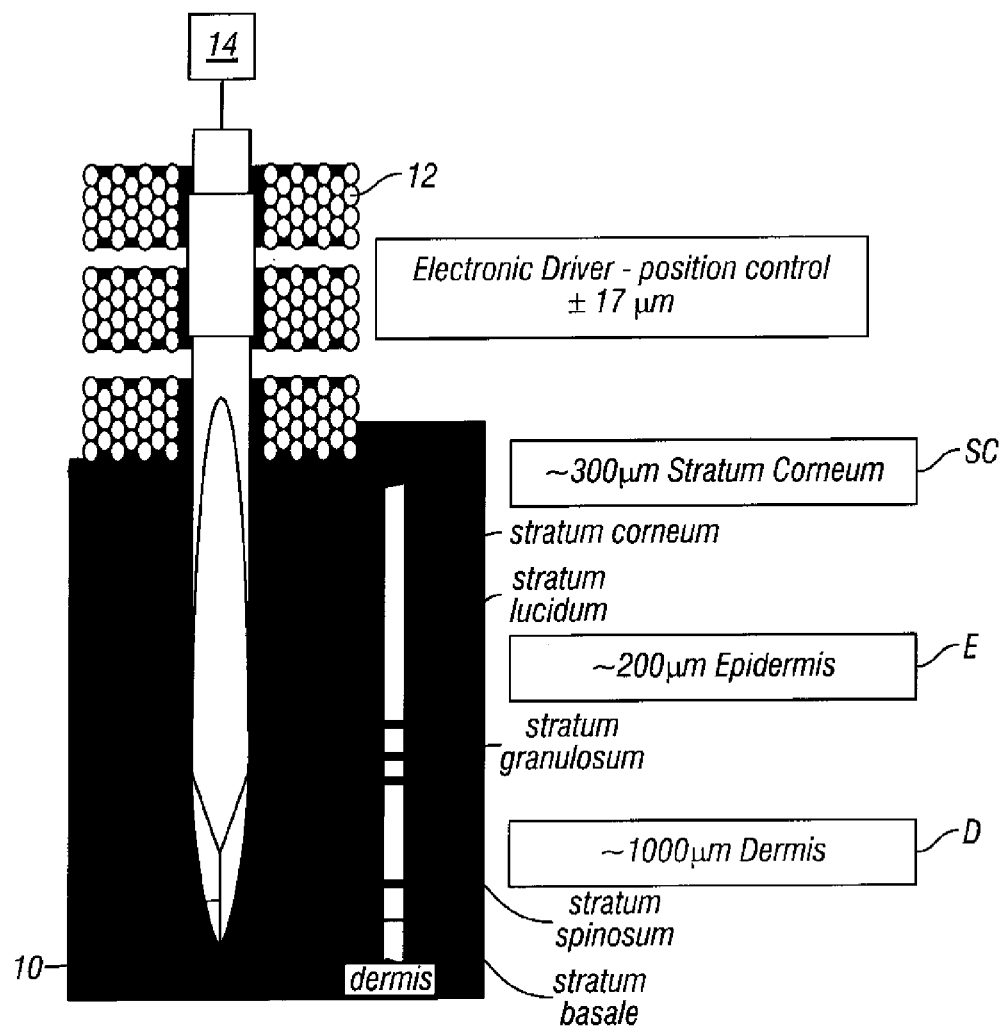
FIG. 1 is a diagram shows a lancet penetrating layers of the skin in a histological section.

It is to be understood that both the foregoing general description and the following detailed description are exemplary and explanatory only and are not restrictive of the invention, as claimed. It should be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

The pain and sufficiency of blood yield of a capillary blood sample from the skin may vary based in part on the efficiency of the cutting device within skin layers. Specifically, the ability to control the lancet trajectory in terms of the velocity profile within the spatial constraints of the skin layers will determine, at least in part, how painless, and how efficient the cutting is.

There is a regional variation in cell type from the surface of the skin down through the epidermis and dermis. As a nonlimiting example, cutting the blood vessels yields blood volumes of about 1-3 µL using lancets of diameters 300 to 400 µm at depths of about 0.1-1.5 mm. It is desirable, in one embodiment, to only penetrate deep enough to reach and cut the required amount of blood vessels for a blood sample. Penetrating too deep causes more pain than necessary, penetrating too shallow does not yield enough blood or no blood. In one embodiment, cutting the capillaries in the superficial reticular layer of the dermis with a 300 µm diameter lancet is sufficient to yield enough blood to fill current state of the art glucose test strips using 0.3-0.5 µL of blood.

In one ideal situation, a painless incision by the lancet would cut enough blood vessels to yield a spontaneous blood sample, which would reach the surface of the tissue for analyte testing for such metabolites as glucose without cutting many nerves or disturbing the elastin fiber net, collagen fibers. Efficient cutting would be defined as controlled lancing for minimal pain to yield a required blood volume for testing at a shallow depth which equates to cutting the capillary mesh in the superficial reticular layer.

Using an electronically driven lancet, (where position and velocity are accurately controlled) the user can fine-tune the cutting process depending on the cell population and distribution in the different layers, for example, based on whether nerves are present or not, or based on the elastin or collagen fiber content orientation or distribution.

Accurate depth control relates to generating a spontaneous blood sample with minimum pain. It is desirable, in one embodiment, to vary the velocity of the cutting lancet based on the cell population. The surface of the skin is comprised of dead or dying cells (the stratum corneum). It is a horny layer, which may vary from 100 µm to 600 µm in thickness, and represents the top layer of the epidermis. The deeper layers of the epidermis can be grouped into 5 different layers, the last of which separates it from the dermis. The epidermis has little innervation compared to the dermis. The distance from the bottom of the stratum corneum to the capillary loops of the dermal papillae is about 300 µm. In one embodiment, using an electric lancet actuator coupled with a position transducer, it is possible to resolve position of the lancet within the skin to an accuracy of ±17 µm. This translates in to over 40 steps through which the velocity can be fed back and controlled. It should be understood, of course, that sensors of other accuracies, as known in the art, may also be used. Embodiments of the invention include devices and methods to control the velocity of the lancet within the different anatomical layers of the skin to achieve the most efficient cutting. Advantages are achieved by use of a miniaturized electronic lancing system for efficiently cutting through the layers of skin by optimizing the velocity profile and using position control feedback mechanism is described.

Referring now to FIG. 1, layers of the skin are shown in this histological section. Skin is composed of various distinct anatomical regions (FIG. 1). The main function of the epidermis E is to protect the body from harmful influences from the environment and against fluid loss. The dermis D is the thick layer of connective tissue to which the epidermis D is attached.

The epidermis E is compsed of an outermost layer is the stratum corneum, which mainly consists of dead keratinized cells. Variations in the thickness of the epidermis (~0.1 mm. in thin skin, 1 mm or more in thick skin) are mainly the result of variations in the thickness of the stratum corneum (SC). The epidermis E composed of stratum lucidum (consisting of several layers of flattened dead cells), stratum granulosum (consisting of a few layers of flattened cells) stratum spinosum (cells are irregularly polygonal and often separated by narrow, translucent clefts), and stratum basale. Stratum basale is the deepest layer or zone of the epidermis and separates the epidermis from the dermis. It consists of a single layer of columnar or cuboidal cells, which rest on the basement membrane. Basal cells are the stem cells of the epidermis.

The dermis D is where capillaries and blood vessels are located and nerves supported by connective tissue including collagen fibers and elastin are found. The collagen fibers give the dermis its strength, the elastin and microfibrils give skin its elasticity. Its deepest part continues into the subcutaneous tissue without a sharply defined boundary making thickness difficult to determine. It is about 1-2 mm for "average" skin.

For a blood sample to reach the surface of the tissue or skin following lancing, several factors come in to play. The lancet may cut through each layer, it may reach the required depth to cut a sufficient number of blood vessels for the desired blood volume, and then the blood may be able to flow up the wound tract created by the lancet and arrive at the surface of the skin. If blood arrives at the surface of the finger without "milking" of the finger, this is called a 'spontaneous' blood sample. Generating a spontaneous blood sample is crucial when interfacing a measurement unit (e.g. test strip) to the lancing event. The lancet penetration may be deep enough that adequate vessels are cut to release the blood, and not too deep that unnecessary pain is generated. Thus accurate depth control is the primary factor controlling a spontaneous blood sample.

Maintaining wound patency is also a factor for achieving a "successful" bleeding event. Many times blood is prevented from flowing upstream the wound channel due to closure of the channel by retraction forces of surrounding elastic fibers, which cause the wound channel to close before the blood can surface. Keeping the wound open and allowing spontaneous blood flow can be achieved by slowly retracting the lancet up the wound channel.

As seen in FIG. 1, the thickness of the stratum corneum SC, epidermis E and dermis D are given for comparison. In one embodiment, the lancet or penetrating member 10 driven along a penetration path by an electronic driver 12, may reach the blood vessels located in the dermis D, and cut enough of them to produce a sample of blood for testing. In one embodiment, the cutting process may be as painless as possible. This may be achieved by a rapid cutting speed and accurate control of depth of penetration.

Figure 2:
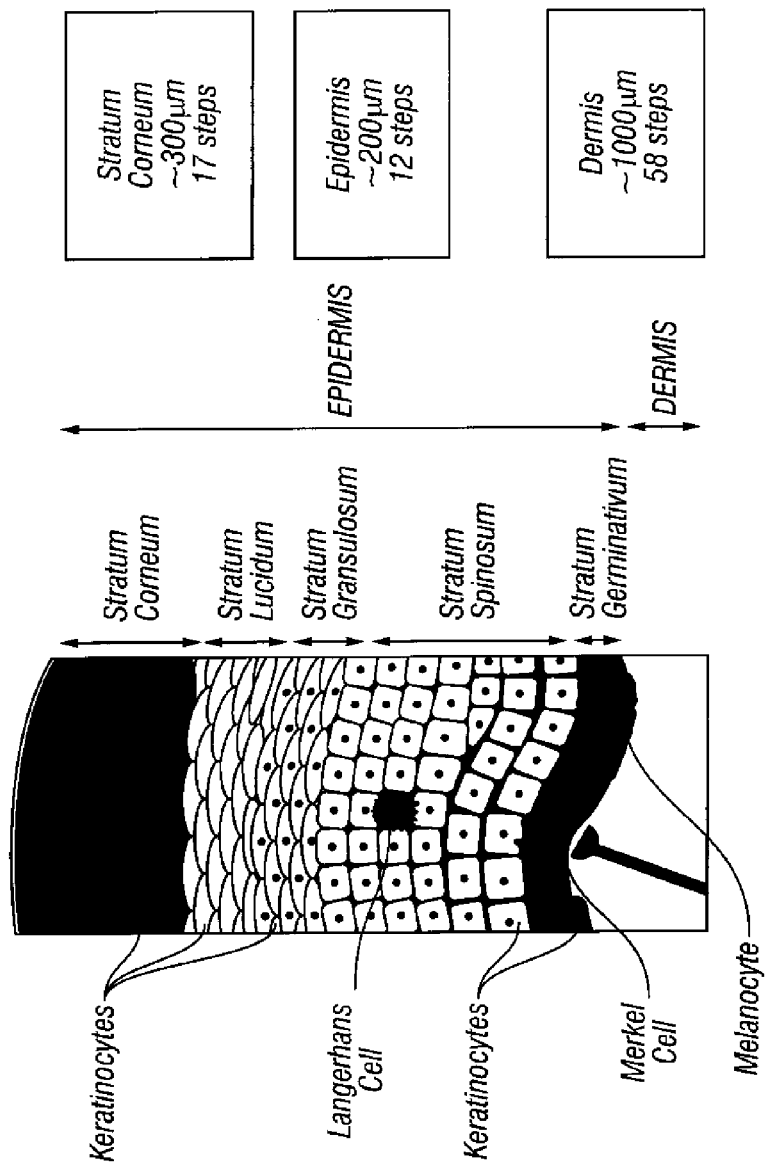
FIG. 2 is a skin anatomy drawing showing the various skin layers with distinct cell types.

The ability to control the lancet or penetrating member trajectory in terms of the velocity profile of the lancet or penetrating member 10 within the spatial constraints of the skin layers may result in less painful, more efficient cutting of the skin. In one embodiment, the user can fine tune the cutting process depending on the skin layer and cell population of the different zones using an electronically driven lancet 10, where position and velocity are accurately controlled i.e. whether nerves are present or not as seen in FIG. 2. Specifically, FIG. 2 shows skin anatomy relevant to capillary blood sampling. The skin layers are comprised of distinct cell types. Variation of lancet velocity based on cell populations in the different layers allows for very precise cutting.

For an electronic or electromechanical lancet driver 12, such as the controllable electronic drivers described in copending U.S. Patent Application Ser. No. 10/127,395, titled "Tissue Penetration Device", operating at a lancing velocity in the range of about 4-10 m/s is possible. This is two to four times faster than the commonly available mechanically actuated devices, (which operate in the range of 1-2 m/s). Ballistic mechanical launcher devices are also not equipped with position feedback mechanisms. Depth control in these devices is usually by an end cap with stepped offsets. The lancet barrel hitting the back of the cap controls the lancet depth. The thicker the offset, the shallower the resulting penetration. Users select the depth they prefer by dialing in the number represented on the device. In one embodiment, penetration settings vary from about 0.5-2.0 mm with steps of about 0.2 mm to 0.4 mm. The accuracy of the depth variation is of the order of±0.1 mm with the selected puncture depth.

As a nonlimiting example, using an electric lancet driver 12 coupled to an optical position sensor 14, velocity of the lancet 10 may be controlled at any stage during the actuation and retraction. In one embodiment, the accuracy of the device in terms of position may be different for the inbound and outbound phase of the movement. Two different types of sensor readings may be applied for the inbound and the outbound. The current embodiment achieves 70 µm accuracy on the inbound phase using a so called "single (falling) edge detection" and 17 µm for the outbound, using a so called "four (rising and falling) edge detection". In this nonlimiting example, the accuracy of the velocity control is within 1% at a speed of 5 m/s.

Figure 3:
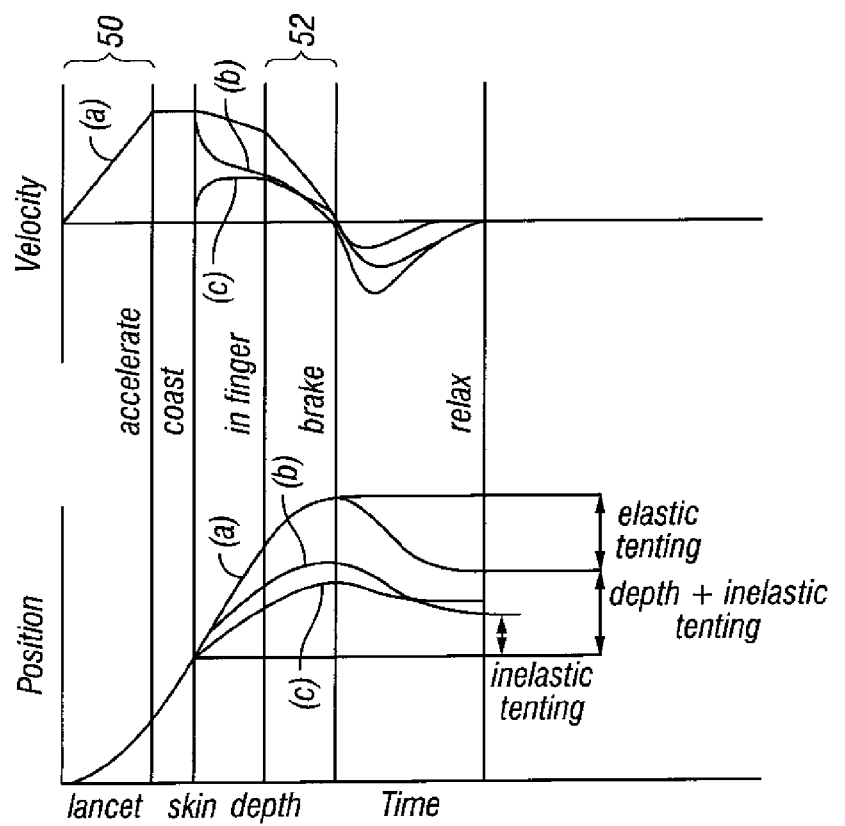
FIG. 3 shows lancet trajectories plotted in terms of velocity and position. Line (a) indicates the lancet position, line (b) indicates the skin position as it interacts with the lancet. Line (c) indicates the actual penetration depth of the lancet within the skin.

Referring now to FIG. 3 for another nonlimiting example, lancet position and velocity during an actuation and retraction event is shown. Lancet trajectories in FIG. 3 are plotted in terms of velocity and position. Line (a) indicates the lancet position, line (b) indicates the skin position as it interacts with the lancet. Line (c) indicates the actual penetration depth of the lancet within the skin. The difference between the elastic tenting or bending of the skin and the lancet position is the actual depth of penetration. Skin tenting can account for up to 100 µm. Inelastic tenting (the fact that the skin does not return to it original position post lancet removal) is on average about 100 µm. The invention focuses on controlling the lancet velocity while on the inbound trajectory in the finger skin.

As seen in FIG. 3, the lancet 10 in one embodiment undergoes an acceleration phase 50 to a specified velocity from where it coasts until it contacts the skin. This velocity may be preset. At this point any type of velocity profile can be defined until it reaches the target depth. There is a braking period 52 included which allows the lancet 10 to come to a complete stop at the selected penetration depth for this embodiment. The lancet 10 is then retracted from the tissue or finger, and returns to the housing.

Figure 4:
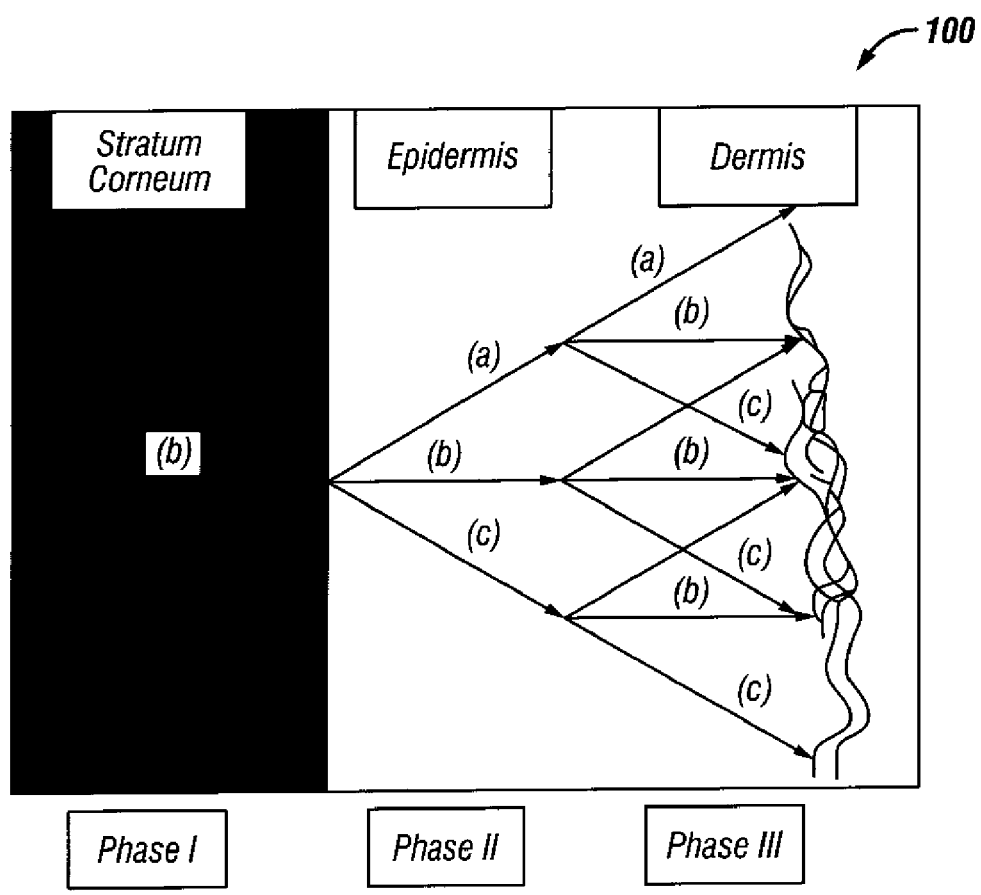
FIG. 4 is a diagram showing variation of lancet velocity through different phases of the inbound trajectory.

Referring now to FIG. 4, the area of interest is the velocity profile 100 while the lancet is cutting through the skin layers in the finger until it reaches a predetermined depth. More specifically, variation of lancet velocity through different phases of the inbound trajectory is shown in FIG. 4. In this embodiment, Phase I corresponds to the stratum corneum, phase 11 to the epidermis and phase III to the dermis. At each phase (and during the phase), the options are to maintain current velocity, increase current velocity or decrease current velocity. Based on the thickness of the stratum corneum, velocity could be monitored and changed in this embodiment at 9 points in the stratum corneum, 6 points in the epidermis, and 29 points in the dermis using the four edge detection algorithm and the 360 strips per inch encoder strip. It should be noted that although the embodiment of the driver discussed herein produces the previously discussed number of monitoring points for a given displacement, other driver and position sensor embodiments may be used that would give higher or lower resolution.

For the purposes of the present discussion for this nonlimiting example, the skin is viewed as having three distinct regions or tissue layers: the stratum corneum SC (Phase I), the epidermis E (Phase II) and the dermis D (Phase II). In one embodiment, the lancet 10 is accelerated to a first desired velocity. This velocity may be predetermined or it may be calculated by the processor during actuation. The processor is also used to control the lancet velocity in tissue. At this velocity, the lancet 10 will impact the skin and initiate cutting through the stratum corneum. The stratum corneum is hard, hence in this embodiment, maximum velocity of the lancet 10 may be employed to efficiently cut through this layer, and this velocity may be maintained constant until the lancet passes through the layer. Power will likely need to be applied to the lancet drive 12 while the lancet is cutting through the stratum corneum in order to maintain the first velocity. Average stratum corneum thickness is about 225 µm. Using a four-edge detection algorithm for the position sensor 14 of this embodiment, the opportunity to verify and feed back velocity information can be carried out at 225/17 or roughly 13 points. In another embodiment accelerating through the stratum corneum following impact may improve cutting efficiency. Acceleration may be possible if the lancet has not reached its target or desired velocity before impact. FIG. 4 shows the result of increasing ((a) arrows), maintaining ((b) arrows) or reducing ((c) arrows) velocity on the lancet trajectory for each of the tissue layers.

On reaching the epidermis E (Phase II), an embodiment of a method may decrease the velocity ((c) arrows) from the first velocity so that tissue compression is reduced in this second tissue layer. Thus the lancet 10, in this nonlimiting example, may have a second desired velocity that is less than the first velocity. The reduced speed in the second tissue layer may reduce the pain experienced by the mechano receptor nerve cells in the dermal layer (third tissue layer). In the absence of tissue compression effects on the dermal layer, however, lancet velocity may be kept constant for efficient cutting (i.e. second velocity may be maintained the same as the first velocity). In another embodiment, velocity may be increased in the second tissue layer from the first velocity.

In Phase III, the lancet or penetrating member 10 may reach the blood vessels and cut them to yield blood. The innervation of this third tissue layer and hence pain perception during lancing could be easily affected by the velocity profile chosen. In one embodiment, a third desired velocity may be chosen. The velocity may be chosen to minimize nerve stimulation while maintaining cutting efficiency. One embodiment would involve reducing velocity from the second velocity to minimize pain, and may increase it just before the blood vessels to be cut. The number of velocity measurement steps possible for the position sensor described above in the dermis is approximately 58. The user would determine the best velocity/cutting profile by usage. The profile with the least amount of pain on lancing, yielding a successful blood sample would be programmable into the device.

Currently users optimize depth settings on mechanical launchers by testing various settings and through usage, settle on a desired setting based on lancing comfort. Embodiments of the device and methods discussed herein provide a variety of velocity profiles (FIG. 4), which can be optimized by the user for controlled lancing, and may include: controlling the cutting speed of a lancet with the lancet within the skin; adjusting the velocity profile of the lancet while the lancet is in the skin based upon the composition of the skin layers; lancing according to precise regional velocity profiles based on variation in cell type from the surface of the skin down through the epidermis and dermis; lancing at a desired velocity through any tissue layer and varying the velocity for each layer. This may include maximum velocity through the stratum corneum, mediation of velocity through epidermis to minimize shock waves to pain sensors in dermis, and mediation of velocity through dermis for efficient cutting of blood vessels without stimulating pain receptors.

Figure 5:
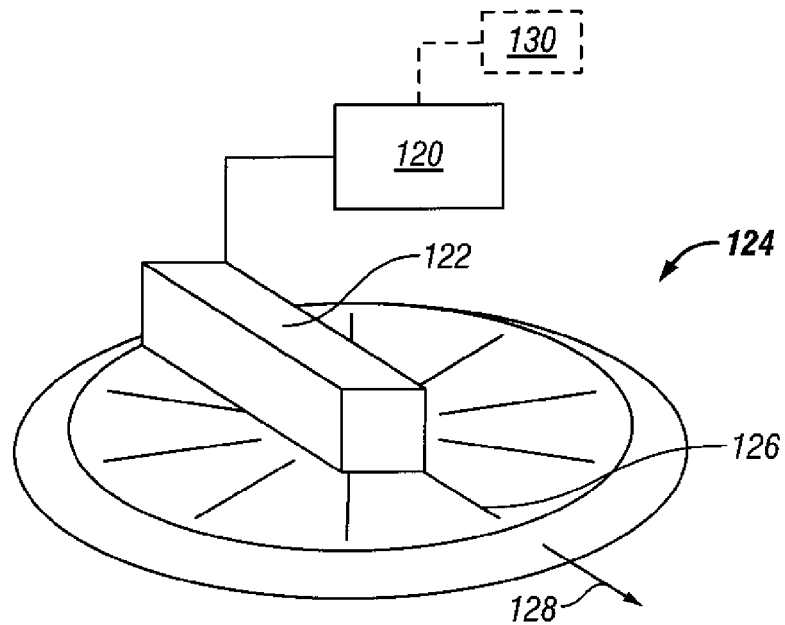
FIG. 5 shows one embodiment of an invention according to the present invention for use with a multiple lancet cartridge.

Referring now to FIG. 5, a processor 120 according to the present invention is used to control the lancet driver 122. As previously discussed, a suitable lancet driver may be found in commonly assigned, copending U.S. patent application Ser. No. 10/127,395 titled "Tissue Penetration Device" filed on Apr. 19, 2002. The lancet or penetrating member driver may be adapted for use with a cartridge 124 holding a plurality of lancets or penetrating members 126 which may be actuated to extend outward as indicated by arrow 128. A suitable cartridge may be found in commonly assigned, copending U.S. patent application Ser. No. 10/324,053 filed on Dec. 18, 2002. The system may also include memory 130 for storing at least one of the following to determine a skin profile: energy consumed per lancing event; stratum corneum hydration; time of day of stratum corneum hydration measurement.

Figure 6:
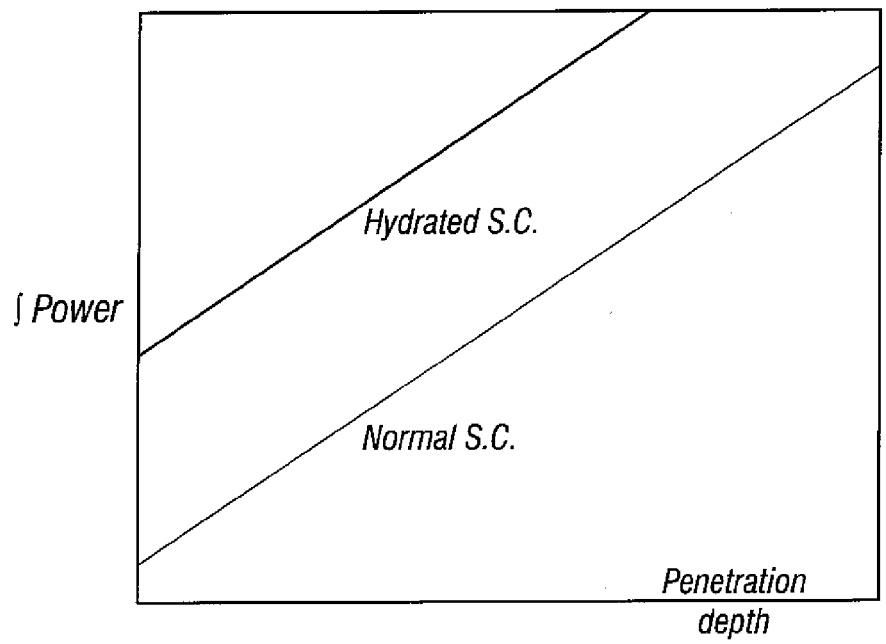
FIG. 6 is a graph showing a difference in power depending on the level of stratum corneum hydration.

Referring now to FIG. 6, the amount of power used to penetrate into the tissue may increase with increased hydration of the stratum corneum. The present invention provides methods for compensating for variation in stratum corneum hydration. Hydration has its strongest effect in the outer layer of the stratum corneum. Studies have shown that coenocytes can swell up to 80% larger on hydration. It is useful to determine what proportion of electrical power consumption is related the change in thickness of stratum corneum from measuring electrical property differences between normal and hydrated stratum corneum. The present invention determines the amount of energy used to achieve a certain penetration depth atvarious states of stratum corneum hydration. By recording a history of penetration energy and the hydration level, the amount of extra energy used during lancing may be attributed to the change in thickness of the stratum corneum brought about by increased or decreased hydration. In one embodiment, the user will adjust penetration depth, lancing velocity, lancing velocity for certain tissue layers, time of day, or to account for in stratum corneum variations due to hydration level.

The pain and efficiency of blood yield of a capillary blood sample from the skin may very well depend on the efficiency of the cutting device within skin layers. The ability to control the lancet trajectory in terms of the velocity profile within the skin layers will determine how painless, and how efficient the cutting is. Using an electronically driven lancet, where position and velocity are accurately controlled the user can fine-tune the cutting process depending on the cell population and distribution in the different zones for efficient, painless and reproducible lancing.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the location of the penetrating member drive device may be varied, relative to the penetrating members or the cartridge. Some other advantages of the disclosed embodiments and features of additional embodiments include: a high number of penetrating members such as 25, 50, 75, 100, 500, or more penetrating members may be put on a disk or cartridge; molded body about a lancet may be used but is not a necessity; manufacturing of multiple penetrating member devices is simplified through the use of cartridges; handling is possible of bare rods metal wires, without any additional structural features, to actuate them into tissue; maintaining extreme (better than 50 micron -lateral- and better than 20 micron vertical) precision in guiding; and storage system for new and used penetrating members, with individual cavities/slots is provided. Any of the dependent claims which follow may be combined with any independent claim which follows.

Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of penetrating tissue comprising:
   using a lancet driver to advance a lancet into said tissue;

advancing said lancet at a first desired velocity in a first layer of tissue;

advancing said lancet at a second desired velocity in a second layer of tissue;

advancing said lancet at a third desired velocity in a third layer of tissue; and creating a wound in the tissue; wherein at least two of the first, the second, the third velocity being different; and wherein the first, the second and the third layer are different tissue layer.

2. The method of claim 1 further comprising using a processor having logic for controlling velocity of the lancet in each layer of tissue.

3. The method of claim 2 wherein said lancet achieves a lancet velocity between about 4 to 10 m/s while in at least one of the layers of tissue.

4. The method of claim 2 wherein said lancet achieves a penetration depth, as measured from a surface of the tissue, of between about 0.5 to about 2.0 mm.

5. The method of claim 2 wherein said second desired velocity is sufficient to minimize nerve stimulation while maintaining cutting efficiency.

6. The method of claim 2 wherein said second velocity is the same as the first velocity.

7. The method of claim 2 wherein said first velocity is at least partially determined based on hydration of the stratum corneum.

8. The method of claim 2 wherein said second velocity is at least partially determined based on hydration of the stratum corneum.

9. The method of claim 2 wherein a four edge algorithm is used to control lancet velocity.

10. The method of claim 2 wherein there are at least 30 different decision points to change lancet velocity during penetration.

11. The method of claim 2 wherein there are at least 30 different decision points to change lancet velocity prior to the lancet reaching a stopped position in the tissue.

12. The method of claim 2 further comprising using a first detection algorithm on a lancet inbound phase and a second detection algorithm on a lancet outbound phase.

13. The method of claim 2 controlling lancet velocity to within 1% at a speed of 5 m/s.

14. The method of claim 2 lancing according to regional velocity profiles based on variation of cell type.

15. The method of claim 2 lancing according to regional velocity, said velocity base on changes of regional cell types and the resistance they provide.

16. The method of claim 2 lancing according to regional velocity profiles based on location to pain sensors.

17. The method of claim 2 wherein position and velocity are determined based on cell population and distribution in the different zones of tissue.

18. The method of claim 2 wherein said lancet has a maximum velocity through a stratum corneum, has a velocity in the epidermis sufficient to reduce shock waves to pain sensor in dermis, and a velocity through in the dermis sufficient for efficient cutting of blood vessels without stimulating pain sensors.

19. The method of claim 1 wherein said penetrating member achieves a penetrating member velocity between about 4 to 10 m/s while in at least one of the layers of tissue.

20. The method of claim 1 wherein said penetrating member achieves a penetration depth, as measured from a surface of the tissue, of between about 0.5 to about 2.0 mm.

21. The method of claim 1 wherein said penetrating member is sufficient to minimize nerve stimulation while maintaining cutting efficiency.

22. The method of claim 1 wherein said second velocity is the same as the first velocity.

23. The method of claim 1 wherein said first velocity is at least partially determined based on hydration of the stratum corneum.

24. The method of claim 1 wherein said second velocity is at least partially determined based on hydration of the stratum corneum.

25. The method of claim 1 wherein a four edge algorithm is used to control penetrating member velocity.

26. The method of claim 1 wherein there are at least 30 different decision points to change penetrating member velocity during penetration.

27. The method of claim 1 wherein there are at least 30 different decision points to change penetrating member velocity prior to reaching.

28. The method of claim 1 further comprising using a first detection algorithm on a penetrating member inbound phase and a second detection algorithm on a penetrating member outbound phase.

29. The method of claim 1 controlling penetrating member velocity to within 1% at a speed of 5 m/s.

30. The method of claim 1 lancing according to regional velocity profiles based on variation of cell type.

31. The method of claim 1 lancing according to regional velocity, said velocity based on changes of regional cell types and the resistance they provide.

32. The method of claim 1 lancing according to regional velocity profiles based on location to pain sensors.

33. The method of claim 1 wherein position and velocity are determined based on cell population and distribution in the different zones of tissue.

34. The method of claim 1 wherein said penetrating member has a maximum velocity through a stratum corneum, has a velocity in the epidermis sufficient to reduce shock waves to pain sensor in dermis, and a velocity through in the dermis sufficient for efficient cutting of blood vessels without stimulating pain sensors.

* * * * *